(12) United States Patent
Gray et al.

(10) Patent No.: US 11,826,018 B2
(45) Date of Patent: Nov. 28, 2023

(54) ROTATABLE MEDICAL DEVICE

(71) Applicant: Boston Scientific Scimed, Inc., Maple Grove, MN (US)

(72) Inventors: Jeff Gray, Sudbury, MA (US); Ryan Wales, Northborough, MA (US); Scott Brechbiel, Acton, MA (US); Paul Smith, Smithfield, RI (US); Richard Mansfield, Sterling, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 128 days.

(21) Appl. No.: 17/166,656

(22) Filed: Feb. 3, 2021

(65) Prior Publication Data
US 2021/0235973 A1     Aug. 5, 2021

Related U.S. Application Data

(60) Provisional application No. 62/969,925, filed on Feb. 4, 2020.

(51) Int. Cl.
*A61B 1/00* (2006.01)
*A61B 1/005* (2006.01)
(Continued)

(52) U.S. Cl.
CPC ........ *A61B 1/00066* (2013.01); *A61B 1/0057* (2013.01); *A61B 1/018* (2013.01);
(Continued)

(58) Field of Classification Search
CPC .............. A61B 1/0052; A61B 1/00066; A61B 1/00087; A61B 1/00137; A61B 1/00105;
(Continued)

(56) References Cited

U.S. PATENT DOCUMENTS 4,705,023 A * 11/1987 Arai ........................ A61B 1/018
600/137
4,750,477 A * 6/1988 Wardle ................... A61B 1/307
600/149
(Continued)

FOREIGN PATENT DOCUMENTS

WO    2008045374 A2    4/2008
WO    2017198673 A1    11/2017

OTHER PUBLICATIONS

International Search Report and Written Opinion dated May 18, 2021 in Application No. PCT/US2021/016386 (13 pages).

*Primary Examiner* — Ryan N Henderson
(74) *Attorney, Agent, or Firm* — Bookoff McAndrews PLLC

(57) ABSTRACT

A medical device comprising a shaft, a handle including a proximal portion and a distal portion, wherein the distal portion is fixed to a proximal portion of the shaft, and a channel extending from the handle into the shaft, wherein the channel includes a proximal channel and a distal channel, the proximal channel being rotatable relative to the distal channel and aligned with the distal channel throughout rotation of the proximal channel, wherein the proximal portion includes the proximal channel and the distal portion includes the distal channel, wherein the distal portion is rotatable relative to the proximal portion of the handle, and the shaft is configured to rotate with the distal portion of the handle.

20 Claims, 7 Drawing Sheets

(51) Int. Cl.
*A61B 1/018* (2006.01)
*A61B 1/267* (2006.01)
*A61M 25/01* (2006.01)

(52) U.S. Cl.
CPC ....... *A61B 1/2676* (2013.01); *A61M 25/0136* (2013.01); *A61M 25/0147* (2013.01)

(58) Field of Classification Search
CPC ....... A61B 1/267; A61B 1/2676; A61B 1/012; A61B 1/018; A61B 1/00064; A61B 1/00121; A61B 1/00071; A61M 25/0136
See application file for complete search history.

(56) References Cited

U.S. PATENT DOCUMENTS

| | | | | |
|---|---|---|---|---|
| 4,972,828 A * | 11/1990 | Ito | ............ | A61B 1/018 600/153 |
| 5,287,845 A * | 2/1994 | Faul | ............ | A61B 1/12 600/156 |
| 5,486,155 A * | 1/1996 | Muller | ............ | A61B 1/00135 600/137 |
| 5,810,715 A * | 9/1998 | Moriyama | ............ | A61B 1/0051 600/141 |
| 5,810,718 A * | 9/1998 | Akiba | ............ | A61B 1/00128 600/156 |
| 7,670,285 B2 * | 3/2010 | Yamaya | ............ | A61B 1/00137 600/154 |
| 8,784,299 B2 * | 7/2014 | Takemoto | ............ | A61B 1/00 604/95.04 |
| 8,911,355 B2 * | 12/2014 | Takeuchi | ............ | F16L 47/32 600/153 |
| 9,498,112 B1 | 11/2016 | Stewart et al. | | |
| 2003/0040657 A1 * | 2/2003 | Yamaya | ............ | A61B 1/00147 600/106 |
| 2006/0063975 A1 * | 3/2006 | Hipp | ............ | A61B 1/00128 600/105 |
| 2006/0276688 A1 * | 12/2006 | Surti | ............ | A61B 1/126 600/154 |
| 2008/0065116 A1 | 3/2008 | Lee et al. | | |
| 2011/0118544 A1 * | 5/2011 | Adams | ............ | A61B 1/015 600/156 |
| 2012/0010464 A1 * | 1/2012 | Adams | ............ | A61B 1/303 600/156 |
| 2015/0025311 A1 * | 1/2015 | Kadan | ............ | A61B 17/3474 600/104 |
| 2016/0249792 A1 * | 9/2016 | Ogawa | ............ | A61B 1/00128 600/153 |
| 2018/0280660 A1 | 10/2018 | Landey et al. | | |
| 2020/0288945 A1 * | 9/2020 | Kaneko | ............ | A61B 1/00071 |

\* cited by examiner

ROTATABLE MEDICAL DEVICE

CROSS-REFERENCE TO RELATED APPLICATIONS

This application claims the benefit of priority from U.S. Provisional Application No. 62/969,925, filed on Feb. 4, 2020, which is incorporated by reference herein in its entirety.

TECHNICAL FIELD

This disclosure relates generally to a medical device including a shaft that is rotatable, relative to the handle. At least some embodiments of the disclosure relate to a medical device having a distal portion of a handle that is rotatable relative to a remaining portion of the handle, where the distal portion of the handle houses and is coupled to the shaft.

BACKGROUND

In certain medical procedures, physicians and/or technicians need to control a bronchoscope (or other scope or medical device) and other medical accessory devices. Depending on a patient's position relative to that of the physician's, the physician controlling the device may need to contort and/or twist his/her body into exaggerated positions to navigate the medical device to the desired anatomical position. As a result, physicians may be placed in less than ideal ergonomic positions, and/or the procedure may suffer.

SUMMARY OF THE DISCLOSURE

According to an example, a medical device may comprise a shaft, a handle including a proximal portion and a distal portion, wherein the distal portion is fixed to a proximal portion of the shaft, and a channel extending from the handle into the shaft, wherein the channel includes a proximal channel and a distal channel, the proximal channel being rotatable relative to the distal channel and aligned with the distal channel throughout rotation of the proximal channel, wherein the proximal portion includes the proximal channel and the distal portion includes the distal channel, wherein the distal portion is rotatable relative to the proximal portion of the handle, and the shaft is configured to rotate with the distal portion of the handle.

In another example, the shaft may surround at least a portion of the distal channel, and the distal channel may be configured to rotate with the shaft and the distal portion of the handle. The distal portion of the handle may be rotatable relative to the proximal portion of the handle in either a clockwise direction or a counterclockwise direction. The rotation of the distal portion of the handle may be limited to a set degree of rotation. The distal portion of the handle may remain stationary relative to the proximal portion of the handle by frictional forces generated between a surface of the distal portion abutting a surface of the proximal portion. The handle may further include a guide, wherein the guide includes a lumen extending along a central axis of the guide, and wherein the lumen is positioned between the proximal channel and the distal channel, and the lumen is aligned with the proximal channel and the distal channel. The guide may be fixed to an inner surface of the proximal portion of the handle. The distal portion of the handle may further include a support along an inner surface of the distal portion of the handle, and the proximal portion of the shaft may be fixed to the support.

In another example, a medical device may further comprise a lock having a first configuration and a second configuration, wherein, in the first configuration of the lock, the distal portion of the handle is stationary relative to the proximal portion of the handle, and, in the second configuration of the lock, the distal portion of the handle is rotatable relative to the proximal portion of the handle. The lock may include a first washer including a pin protruding proximally, wherein the distal channel extends through the first washer via an opening of the first washer, a second washer including a plurality of openings each configured to receive the pin, and a spring coupling a distal surface of the first washer to a base. In the first configuration of the lock, the first washer may be spring-biased towards the second washer so that the pin of the first washer is engaged with one of the plurality of openings of the second washer, and wherein, the second configuration of the lock, the first washer may be spaced proximally from the second washer, compressing the spring, and so the pin is disengaged from all of the plurality of openings. The lock may further include a tube, wherein the tube extends through openings of the first washer and the second washer, wherein the tube sheaths over at least a portion of the distal channel, and wherein the first washer is configured to translate over the tube.

In another example, the medical device may further comprise a first steering wire and a first gyro holding the first steering wire, wherein the first gyro includes a proximal gyro and a distal gyro, and wherein the distal gyro is interlocked with the proximal gyro so that the distal gyro is rotatable about the distal channel or the proximal channel, relative to the proximal gyro. The first steering wire may include a proximal wire and a distal wire, wherein a distal end of the proximal wire is coupled to a first enlargement, and a proximal end of the distal wire is coupled to a second enlargement, wherein the first enlargement is anchored to the proximal gyro and the second enlargement is anchored to the distal gyro. The distal wire may configured to be pulled when the proximal wire is pulled via an actuation device.

According to an example, a medical device may comprise a shaft, a handle connected to a proximal portion of the shaft, and a channel extending from the handle into the shaft, wherein the channel is rotatable relative to the handle, and wherein a side wall of the channel includes an opening at a portion of the channel housed in the handle, wherein the handle defines a lumen in fluid communication with the opening of the channel, and wherein a proximal end of the lumen is configured for fluid communication with a suctioning source. The opening may be sealed from portions of the handle by a first seal and a second seal. The side wall of the channel may include a plurality of circumferentially distributed openings.

According to an example, a method of positioning a shaft of a medical device, wherein the medical device further comprises a handle including a proximal portion and a distal portion rotatably attached to the proximal portion, and a channel extending from the second portion into a the shaft, wherein a proximal portion of the shaft is fixed to the distal portion of the handle, may comprise inserting a distal end of a shaft of the medical device into a body of a subject, and after the insertion step, rotating the distal portion of the handle, the shaft, and the channel relative to the proximal portion of the handle.

In another example, the method may further comprise, after the insertion step, unlocking the distal portion of the handle from the proximal portion of the handle, rotating the distal portion of the handle, the shaft, and the channel relative to the proximal portion of the handle, and locking the distal portion of the handle to the proximal portion of the handle.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Figure 1A:
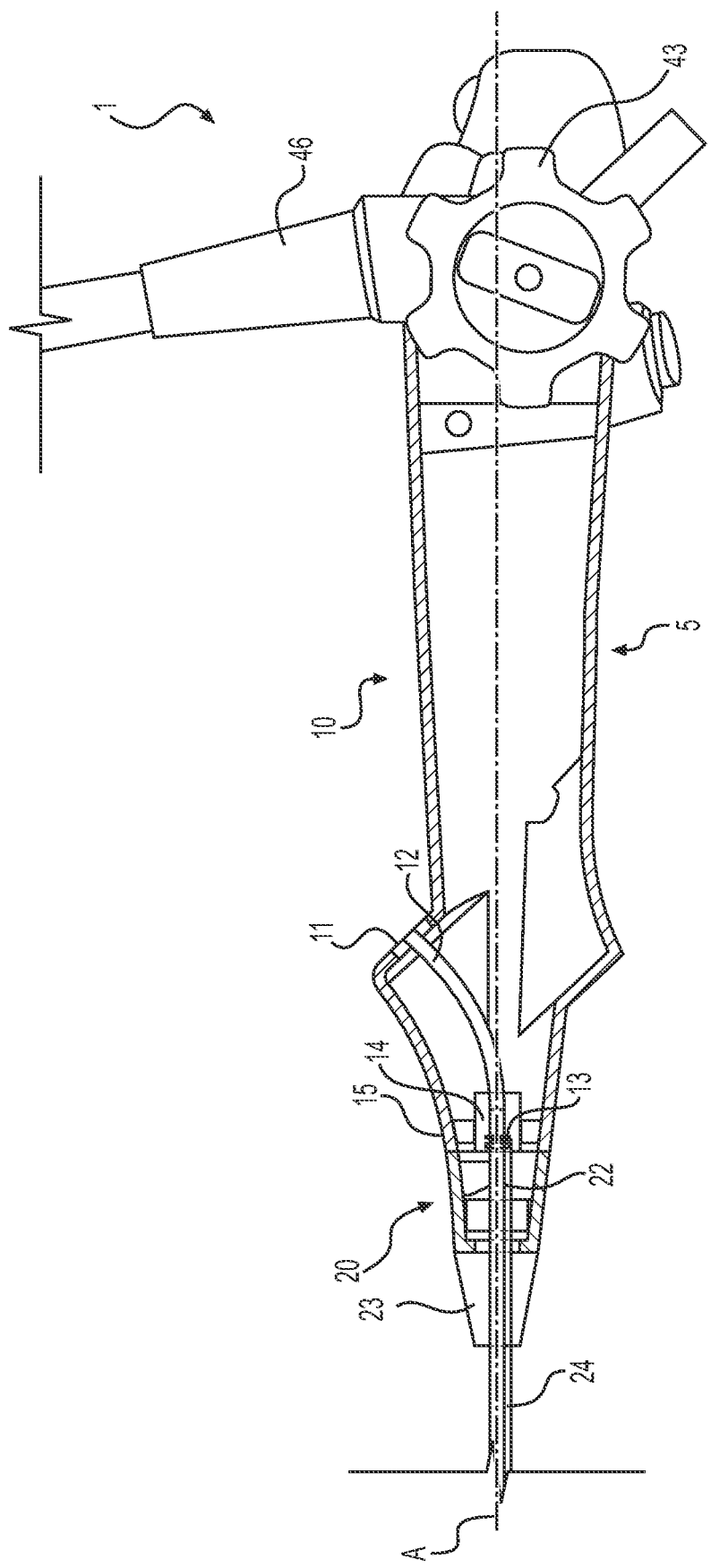
FIG. 1A is a cross-sectional view of a medical device, according to an embodiment.

Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., a patient). By contrast, the term "proximal" refers to a portion closest to the user when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately," are used to indicate a possible variation of ±10% in a stated value or characteristic.

Embodiments of the disclosure may solve one or more of the limitations in the art. The scope of the disclosure, however, is defined by the attached claims and not the ability to solve a specific problem. The disclosure is drawn to medical devices including a shaft, which may be rotatable relative to a handle of the medical device. The medical devices can be, as examples, any scope (e.g., bronchoscope, duodenoscope, endoscope, colonoscope, ureteroscope, etc.), catheter, tool, instrument, or the like, having a shaft that extends distally from a handle. In embodiments, medical devices include a handle having a distal portion rotatable clockwise or counter-clockwise relative to a proximal portion of the handle. The medical devices further include a shaft fixedly coupled to and housed within the distal portion of the handle. Thus, as the distal portion of the handle is rotated relative to the proximal portion of the handle, the shaft simultaneously rotates likewise. The distal portion of a handle may be in one of two states or configurations. In a first state, the distal portion may remain stationary, relative to the proximal portion of the handle. In a second state, the distal portion of the handle may be rotating or capable of rotating, relative to the proximal portion of the handle. Alternatively, the proximal portion of the handle may be rotating or capable of rotating, relative to said distal portion. The shaft of the medical device rotates or remains stationary, in accordance with the distal portion of the handle.

Embodiments of medical devices of the disclosure may employ any suitable means, e.g., friction, a locking/unlocking mechanism, etc., to place or maintain the distal portion of a handle in one of the two states described above. Moreover, such medical devices may provide a user the option of rotating the distal portion of the handle (and thus, the shaft) in-procedure, via any suitable manner, e.g., by hand, mechanically, electrically, etc., and an option of maintaining the distal portion of the handle stationary in its current rotational position relative to a remainder of the device. Thus, a user of the device may comfortably access, view, and/or perform a therapeutic/diagnostic procedure at intended target sites, via rotation of the distal portion of the handle and the shaft, without having to twist and contort his/her wrists or other parts of the body, regardless of a patient's position relative to the user.

Referring to FIG. 1A, a medical device 1, e.g., a bronchoscope, according to an embodiment is shown. Medical device 1 includes a flexible shaft 24 (e.g., a catheter) and a handle 5 connected to a proximal end of flexible shaft 24. Handle 5, or some other device for actuating or controlling medical device 1 and any tools or devices associated with medical device 1, includes an actuating device 43. Actuating device 43 controls articulation of flexible shaft 24, and/or an articulation joint at a distal end of flexible shaft 24, in multiple directions. Device 43 may be, for example, a rotatable knob that rotates about its axis to push/pull actuating elements, e.g., steering wires (not shown). The actuating elements, such as cables or wires suitable for medical procedures (e.g., medical grade plastic or metal), extend distally from a proximal end of medical device 1 and connect to a distal portion of flexible shaft 24 to control movement thereof. Alternatively, or additionally, a user may operate actuating elements independently of handle 5. Distal ends of actuating elements may extend through flexible shaft 24 and terminate at an articulation joint and/or a distal tip of flexible shaft 24. For example, one or more actuating elements may be connected to an articulation joint, and actuation of actuating elements may control the articulation joint or the distal end of flexible shaft 24 to move in multiple directions (e.g. up/down and or left/right).

In addition, one or more electrical cables (not shown) may extend from the proximal end of medical device 1 to the distal end of flexible shaft 24 and may provide electrical controls to imaging, lighting, and/or other electrical devices at the distal end of flexible shaft 24, and may transmit imaging signals from the distal end of flexible shaft 24 proximally to be processed and/or displayed on a display. Handle 5 may also include ports 11, 46 for introducing and/or removing tools, fluids, or other materials from the patient. Port 11 may be used to introduce tools, via a working channel 12. Port 46 may be connected to an umbilicus for introducing fluid, suction, and/or wiring for electronic components. Furthermore, medical device 1 may further include a strain relief 23 that is attached to a distal end of handle 5. Strain relief 23 may be a cover of any suitable soft material that tapers distally and has an opening for shaft 24 at its distal end. Strain relief 23 is not particularly limited, and may assist in preventing shaft 24 from kinking.

Figure 1B:
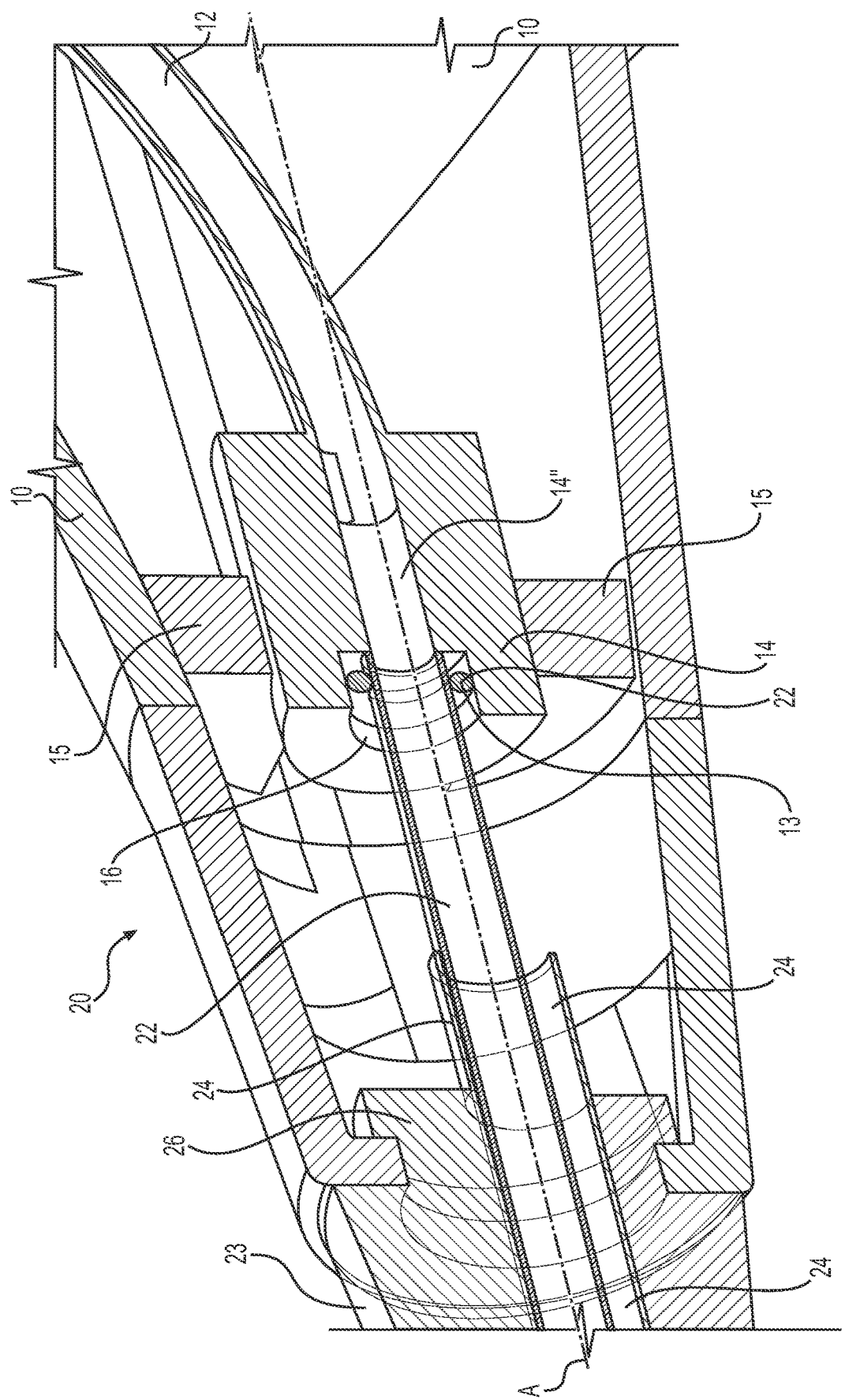
FIG. 1B is a cross-sectional view of a distal portion of the handle of the medical device of FIG. 1A.

Referring to FIGS. 1A and 1B, handle 5 is discussed in further detail below. Handle 5 includes a proximal portion 10 and a rotatable distal portion 20. Distal portion 20 is a discrete, separate component from proximal portion 10. Thus, in some embodiments, handle 5 is not a single piece, and is instead two distinct pieces, proximal portion 10 and distal portion 20. Distal portion 20 is rotatably attached to proximal portion 10, so that portions 10 and 20 are adjacent to one another.

Proximal portion 10 may be of any suitable shape configured for handling or gripping by a user, and may also be any suitable material, e.g., plastic, steel, etc. Proximal portion 10 includes actuating device 43 and ports 46, 11, which are discussed above. As indicated above, proximal portion 10 may be the portion of handle 5 that is configured to be connected to additional wirings and tools, via ports 46 and 11. Port 11 may lead to proximal working channel 12, through which various tools may be introduced.

Proximal working channel 12 may be of any suitable form, and is not particularly limited. For example, in some embodiments, proximal working channel 12 may be a tube, coupled to port 11 and flexible and/or shaped to accommodate the shape of proximal portion 10. In other embodiments, a hollow, tubular channel may be molded within proximal portion 10 to form proximal working channel 12, which may be of any suitable material, e.g., plastic, steel, etc. Channel 12 may be of any suitable diameter or length. A distal portion of channel 12 transitions into a lumen 14' of a guide 14. Guide 14 may be molded with channel 12, as an integral unit. Guide 14 is tubular/cylindrical in shape, and includes lumen 14'. Lumen 14' extends along the central axis of guide 14. Lumen 14' has a diameter that is equal or about equal the diameter of channel 12. Guide 14 may be a molded feature that is anchored within proximal portion 10, via supports 15 extending from the inner surfaces of proximal portion 10 to guide 14. Supports 15 may also be molded features or supports inserted within proximal portion 10. Supports 15 may also include suitable openings or channels to allow any wires and/or suction or irrigation tubing to pass through supports 15, and toward the distal end of shaft 24. Furthermore, device 1 may also define spaces within portions 10 and 20 to allow the same.

Guide 14 and lumen 14' serve as a transition between the distal end of channel 12 of proximal portion 10 and the proximal end of a distal working channel 22 of distal portion 20. A distal end of guide 14 includes a circular void or recess 16 to accommodate a sealing ring 13. Ring 13 (e.g. an O-ring) fits around distal working channel 22. Thus, the diameter of the space within ring 13 may be of the same or about the same diameter as an outer diameter of working channel 22. However, ring 13 fits around channel 22 so that channel 22 may still rotate within ring 13. Alternatively, ring 13 and channel 22 may rotate together within recess 16. Ring 13 may be of any suitable material that allows for it to seal around distal channel 22 and provide for a centering of a proximal end of channel 22 within recess 16 of guide 14. Thus, in view of the above, proximal channel 12, lumen 14', and distal channel 22 remain in direct alignment, without any offset.

Distal portion 20 includes a proximal portion of distal working channel 22. Distal working channel 22, like proximal channel 12, may be of any suitable form. For example, channel 22 may be a tube extending from the end of lumen 14' of guide 14, as described above, to the distal end of shaft 24. Regardless of form, the diameter of channel 22 is the same or about the same as channel 12. In other embodiments, the diameter of channel 22 may be less than or greater than the diameter of channel 12. Furthermore, as discussed above, proximal channel 12 leads to and is in fluid communication with lumen 14', which leads to and is in fluid communication with distal channel 22.

Distal portion 20 further includes a proximal portion of shaft 24, and a clamp 26. Shaft 24 may be a tubing of any suitable length that encompasses at least a portion of, or all of, distal working channel 22, and extends from distal portion 20 to the distal end of medical device 1. Shaft 24 may be a tubing of any suitable material that is flexible. The diameter of shaft 24 is not particularly limited, so long as said diameter may accommodate distal working channel 22 and any desired wires, suction/irrigation tubing, etc. Clamp 26 is a circular clamp/opening that is molded as part of distal portion 20. Clamp 26 is configured to hold/clamp a proximal portion of shaft 24, so that shaft 24 is fixed to distal portion 20. In view of such configuration, the opening of clamp 26 has a diameter that is the same or about the same as the outer diameter of shaft 24. Additional means for securing clamp 26 to shaft 24 may be used, including adhesives, welding, etc. Thus, the proximal portion of shaft 24 is fixedly clamped to distal portion 20, so that shaft 24 (and working channel 22) rotates, as distal handle portion 20 rotates clockwise or counter-clockwise, relative to proximal handle portion 10. At least a portion of distal working channel 22 may be fixed to shaft 24 (via adhesives, welding, etc.), so they may rotate simultaneously.

As noted above, distal portion 20 is rotatably attached to proximal portion 10. Portions 10, 20 abut one another and are flush against one another. The abutting ends of portions 10, 20 are circular and have a same diameter. The means by which distal portion 20 is rotatably attached to proximal portion 10 is not particularly limited, and both portions 10, 20 may include any suitable coupling components/elements (not shown). For example, a proximal surface of distal portion 20 may engage with a distal surface of proximal portion 10 via an anchor/slot coupling mechanism that prevents detachment of portions 10 and 20. In such an example, a distal surface of proximal portion 10 may have a recess extending circumferentially throughout said distal surface, and a proximal surface of distal portion 10 may have a proximally-protruding component/feature, configured to be securely slotted within said recess. In an alternative example, the distal surface of proximal portion 10 may have a distally-protruding feature, while the proximal surface of distal portion 20 includes a recess. However, the attachment between distal portion 20 and proximal portion 10 is not limited as described, and may employ other suitable means.

Distal portion 20 may also be attached to proximal portion 10, so that distal portion 20 is limited in its degree of rotation, e.g., approximately 90°, 120°, 180°, etc., relative to proximal portion 10. Thus, in such examples, coupling components of distal portion 20 and proximal portion 10 may include additional means to limit the rotation of distal portion 20. For example, stops may be positioned at predetermined or selected positions within the previously discussed recesses, thereby inhibiting rotation of distal portion 20 past said stops, due to contact between the protruding features and the stops. However, again, the coupling means is not limited as described, and may employ other suitable components/features to limit distal a degree of rotation of portion 20.

Distal portion 20 and working channel 22 rotate about central axis A of distal working channel 22. Channel 22 therefore maintains direct alignment with lumen 14 and proximal channel 12, throughout the rotation of distal portion 20. Thus, accessory devices or tools extending through both channels 12 and 22 are protected from any damage, e.g., pinching, as distal channel 22 rotates (by rotation of distal portion 20), relative to proximal channel 12.

As discussed above, distal portion 20 may remain in a stationary state or configuration, relative to proximal portion 10. To remain stationary, distal portion 20 or at least the surface of distal portion 20 abutting proximal portion 10 may be of any suitable frictious material, thereby inhibiting undesired movement of distal portion 20 while abutting proximal portion 10. To enhance friction between both portions 10 and 20, proximal portion 10, or at least the surface of proximal portion 10 abutting distal portion 20, may also be of any suitable frictious material. Frictional forces generated between distal portion 20 and proximal portion 10 may be of a sufficient degree to inhibit undesired rotation of distal portion 20, relative to proximal portion 10. However, said frictional forces may not be greater than the ordinary torsional forces applied by a user of medical device 1, so that distal portion 20 may be rotated as desired by said user.

Referring to FIGS. 1A-1B, an example of how medical device 1 may be used is further discussed below. The distal end of shaft 24 of medical device 1 may be delivered into the body of a subject, adjacent to an intended target site. The delivery may be via a natural body orifice, such as the mouth, nose, anus, etc. Imaging associated with medical device 1, via any suitable image processing device, may assist in positioning of the distal end of shaft 24. Depending on the position of the subject and/or the intended target site relative to medical device 1 and/or a user of medical device 1, the user may choose to rotate shaft 24 relative to handle 5. To rotate shaft 24, the user may rotate distal portion 20 of handle 5 relative to proximal portion 10 by applying a torsional force greater than the frictional force between portions 10 and 20. The user may rotate distal portion 20 (and shaft 24) to allow the user's handling of handle 5 in a more ergonomic position, or for various other reasons. Thus, a user may rotate shaft 24 (via rotation of distal portion 20) or proximal portion 10 of handle 5, relative to the other, to any desired degree.

Figure 2A:
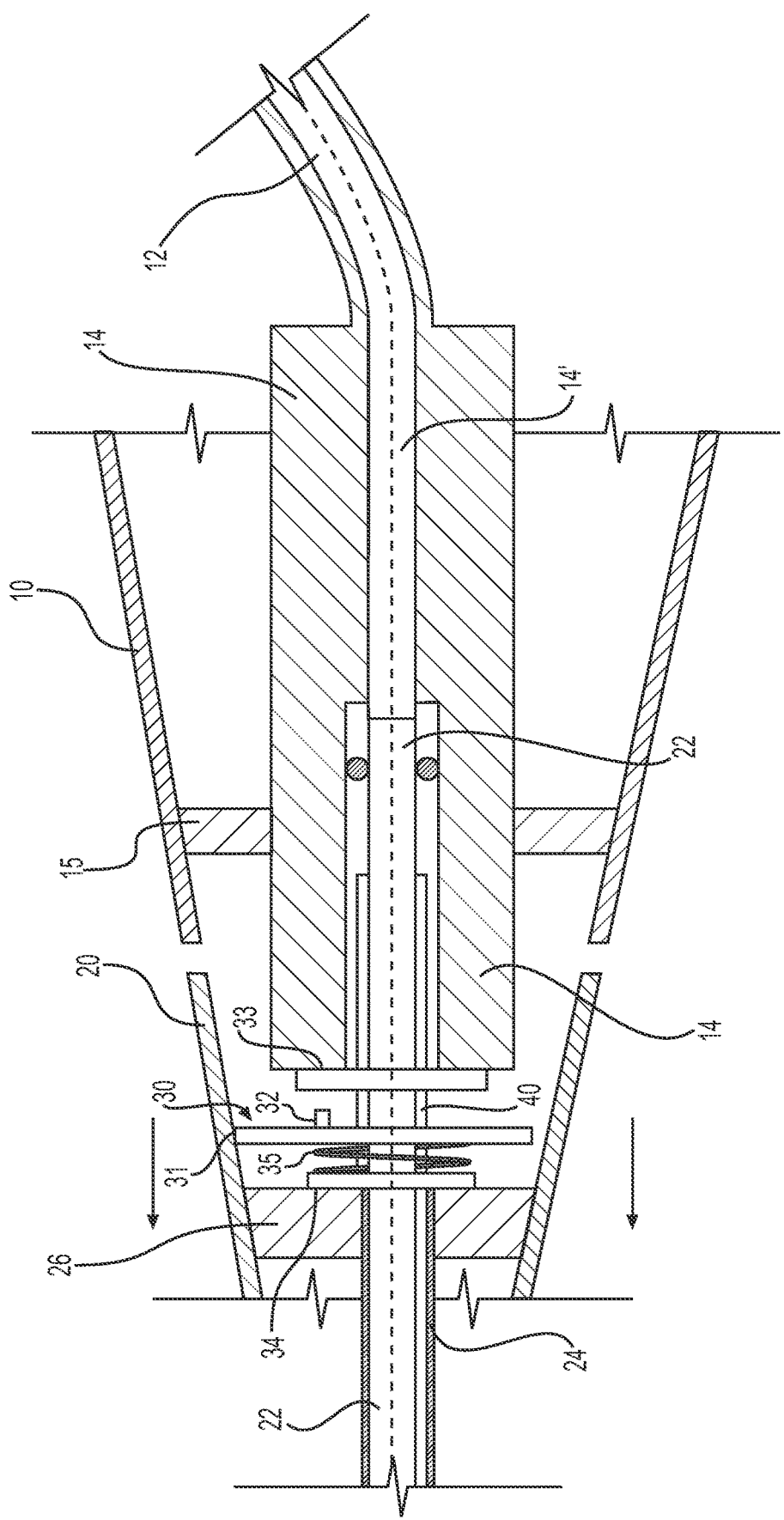
FIG. 2A is a cross-sectional view of a portion of a medical device, according to another embodiment.
Figure 2C:
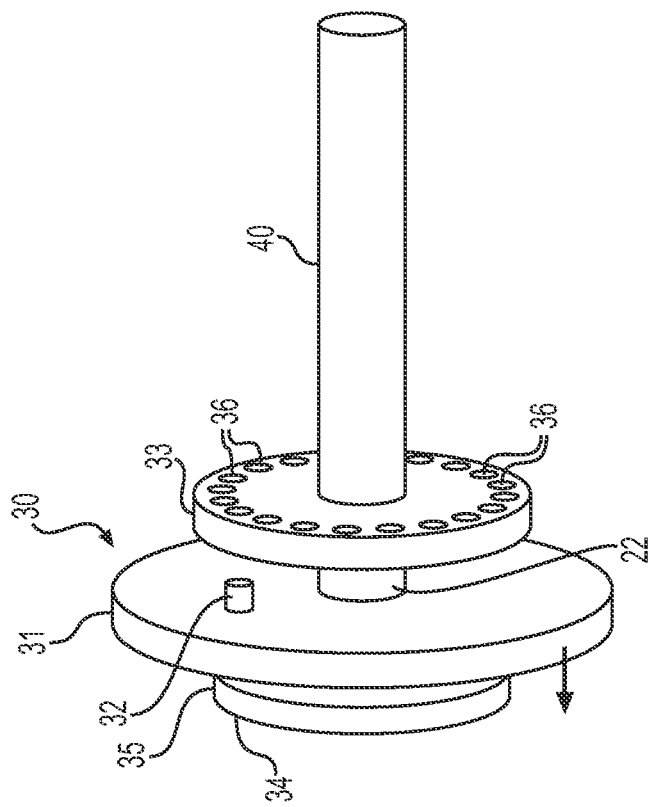
FIG. 2C is a perspective view of the locking mechanism of the medical device of FIG. 2A.
Figure 2B:
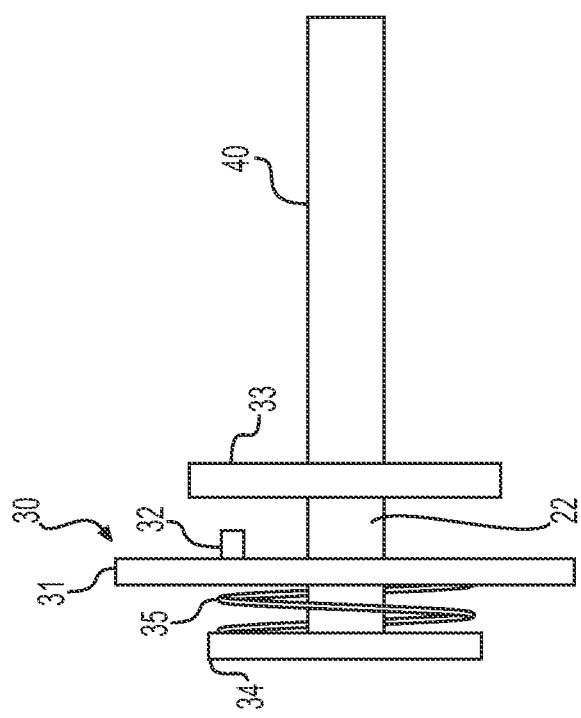
FIG. 2B is a side view of the locking mechanism of the medical device of FIG. 2A.

Medical device 1', as shown in FIG. 2A, is similar to device 1 in many respects. Like reference numerals refer to like parts. Differences between device 1 and device 1' will be described below. Device 1' further includes a lock 30. Lock 30 may include a configuration (e.g. a locked configuration) in which distal portion 20 and shaft 24 may be freely rotatable in any direction (clockwise or counterclockwise), relative to proximal portion 10, and another configuration (e.g. an unlocked configuration) in which distal portion 20 and shaft 24 remain stationary and are not rotatable relative to proximal portion 10. Referring to FIGS. 2A-2C, lock 30 includes a slideable locking washer 31 having a locking pin 32, a receiving washer 33 configured to engage with locking washer 31 and pin 32, a base washer 34, and a spring 35 coupling locking washer 31 to base washer 34. Lock 30 is positioned so that it is distal to guide 14, and channel 22 extends through the central openings along the axes of washers 31, 33, and 34. Lock 30 further includes a center tube 40, also extending through the central openings along the axes of washers 31 and 33. Tube 40 is hollow and sheaths over the portion of channel 22 extending from guide 14 to washer 34. Thus, a portion of tube 40 is sheathed within recess 16 of guide 14. Tube 40 may be fixed to washer 31 so that tube 40 may rotate or slide linearly along with washer 31, as further described below. However, tube 40 may not be fixed to washer 33 so that tube 40 may rotate and slide linearly relative to washer 33. The distal end of tube 40 is fixed to washer 34.

Locking washer 31 is circular/disk-like in shape, but is not limited thereto. The dimensions of washer 31 are not particularly limited, so long as it may be fixed within distal portion 20. Locking washer 31 may be fitted around tube 40 via a central opening, so that washer 31 may be able to slide linearly over tube 40. Locking washer 31 includes locking pin 32, which may be a pin protruding proximally. Pin 32 is located on the proximal surface of washer 31, at a location from which pin 32 may engage one of the receiving holes 36 of receiving washer 33 (described in further detail below). The length and diameter of pin 31 are not particularly limited so long as pin 32 may engage with said receiving holes 36. Similarly, washer 33 is also circular/disk-like in shape, but not limited thereto. In device 1', washer 33 is of a smaller diameter than washer 31. However, the dimensions, e.g., diameter, of washer 33 are not particularly limited. Washer 33 may be fitted around tube 40 via a central opening of washer 33, so that tube 40 may slide and/or rotate about its central axis, relative to washer 33 and proximal portion 10. Washer 33, which is proximal and adjacent to washer 31, includes a plurality of receiving holes 36 on its distal surface. Holes 36 may extend completely through a thickness of washer 33 or partially through washer 33 (e.g. as a recess). Holes 36 may have shapes and widths/diameters that accommodate pin 32 of washer 31. Receiving holes 36 may be distributed circumferentially and evenly about the center point of washer 33. The number of receiving holes 36 is not particularly limited. Base washer 33 is also circular/disk-like in shape, but not limited thereto. The dimensions of washer 33 are also not particularly limited, so long as it may be fixed within distal portion 20. In device 1', a portion of the proximal surface of washer 33 is fixed to the distal end of guide 14 which is within distal portion 20. Washer 33 therefore does not rotate with distal handle portion 20. However, washer 33 is not limited to being fixed to the distal end of guide 14. Washer 33 may also be fixed to other portions or components within proximal portion 10, so that washer 33 does not rotate with distal portion 20. Washer 34 is distal to locking washer 31, and thus, is the distalmost end of lock 30. Spring 35 is positioned between washer 34 and locking washer 31, as it couples the proximal surface of washer 34 to the distal surface of locking washer 31. The distal surface of washer 34 is fixed to the proximal surface of clamp 26. Thus, washer 34 may serve as a fixed base from which locking washer 31 may slide linearly over tube 40, via compression or extension of spring 34. Washers 34 and 31, and spring 35 will rotate with distal handle portion 20.

As discussed above, the distal surface of washer 31 is coupled to base washer 33 via spring 34. As a result, washer 31, of distal portion 20, may be spring-biased to engage with washer 33, via pin 32 and one of holes 36. As previously noted, washer 33 is fixed to guide 14, which is anchored to proximal portion 10 via supports 15. Thus, lock 30 may be defaulted into a locked configuration, thereby inhibiting any rotation of distal portion 20 (and shaft 24) or proximal portion 10, relative to the other.

To transition lock 30 from its default, locked configuration to an unlocked configuration (shown in FIG. 2A), a force pulling distal portion 20 distally may be applied (as indicated by the directional arrows). The connection between distal portion 20 and proximal portion 10 permits some relative translation between them along axis A. This is illustrated by the gaps between distal portion 20 and proximal portion 10, while lock 30 is in the unlocked configuration. For example, the protruding portion(s) and recess(es) or facing surfaces of proximal portion 10 and distal portion 20 mentioned above (not shown) may be configured to permit relative translation. The pulling force disengages locking washer 31 from receiving washer 33 of proximal portion 10. Pin 32 of washer 31 retracts outside of one of openings 36 of washer 31. The pulling force may be applied via any suitable manner, e.g., by hand, mechanically, electrically, etc. While disengaged, distal portion 20 (and shaft 24 which is fixed to portion 20) or proximal portion 10 may freely rotate clockwise or counter-clockwise, relative to the other. Release of the applied force may revert locking washer 31 to its original position, in which it abuts and is engaged with washer 33. If washer 31 fails to engage with washer 33 due to misalignment between pin 32 and one of holes 36 of washer 33, further rotation may occur until alignment and engagement is established.

Medical device 1' may be used in a similar manner as medical device 1, except a user may pull on distal portion 20 distally to unlock lock 30, rotate distal portion 20 (and shaft 24) or proximal portion 10, relative to the other, to a desired degree, and release distal portion 20 to revert lock 30 into a locked configuration.

Figure 3A:
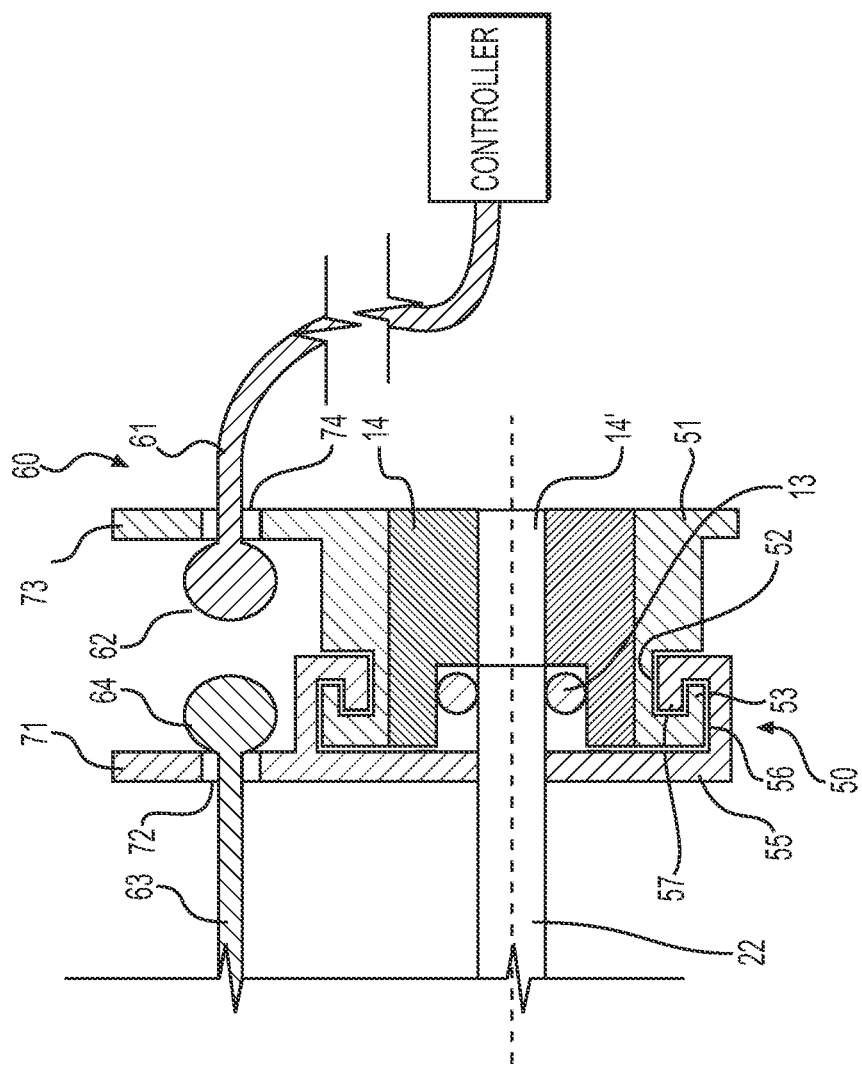
FIG. 3A is a cross-sectional view of a rotatable gyro of a medical device, according to an embodiment.

FIG. 3A illustrates a rotatable gyro 50 that may be included in medical device embodiments, including devices 1, 1' described above. As shown, rotatable gyro 50 surrounds a portion of guide 14 and working channel 22, and also holds a steering wire 60. Gyro 50 may be fitted around the area in which lumen 14' and working channel 22 meet. However, gyro 50 is not limited to such a position, and may also be fitted around, for example, portions of guide 14 within proximal portion 10. Furthermore, it is noted that the presence of gyro 50 and lock 30 in a medical device handle is not mutually exclusive. In some examples, a handle may include gyro 50 fitted around guide 14 and channel 22, and lock 30 also fitted around channel 22.

Each steering wire of a conventional medical device (e.g. a scope) is a single piece routed from the handle to the distal end of a shaft. However, rotation of such steering wires, while rotating the shaft, may result in damage to the steering wires due to the twisting from rotation. To address such a concern, steering wire 60 is of two separate, decoupled wires, proximal wire 61 and distal wire 63, to help enable rotation of distal portion 20 (and shaft 24) without damaging steering wire 60, as described above. The proximal end of proximal wire 61 may be connected to any suitable controller, e.g., device 43 shown in FIG. 1. The distal end of proximal wire 61 is connected to, or integral with, a first termination/ferrule ball 62. The distal end of distal wire 63 connects to the distal end of shaft 24 to control articulation thereof. The proximal end of distal wire 63 is connected to, or integral with, a second termination/ferrule ball 64. Balls 62 and 64 may be of any suitable material, e.g., lead, and is not particularly limited. Alternatively, each ball 62, 64 may be a machined or heat treated end of corresponding wire 61, 63. Furthermore, ball 62, 64 are not particularly limited to being balls, and may be any suitable enlargement. Similarly, wires 61 and 63 are not particularly limited, and may be any suitable cables or wires used for medical procedures (e.g., medical grade plastic or metal).

Gyro 50 includes a proximal gyro 51 and a distal gyro 55, which are rotatably interlinked with one another. Proximal gyro 51 is a structure surrounding guide 14 and holding proximal wire 61. Distal gyro 55 is a structure surrounding distal working channel 22 and holding distal wire 63. Distal gyro 55 may be fixed around channel 22 so that it may be rotatable with channel 22, relative to proximal gyro 51. Proximal gyro 51 may be fixed to guide 14. Proximal gyro 51 includes a recess 52, and a flange 53 that protrudes proximally, thereby partially covering recess 51. Proximal gyro 51 further includes a flange 73 that is proximal to recess 52, and protrudes radially outward, relative to the remainder of proximal gyro 51. The distance by which flange 73 protrudes is not particularly limited, so long as it may be accommodated within device 1". Flange 73 includes a channel 74 at about the midpoint of its radial protrusion. Channel 74 runs parallel or about parallel to a longitudinal axis of guide 14. The width of channel 74 may be such that it accommodates for proximal wire 61, but is narrower than the diameter of first ball 62, which is distal to channel 74. Thus, channel 74 holds proximal wire 61 while also anchoring first ball 62, so that proximal wire 61 is inhibited from slipping out of channel 74 when pulled proximally. Distal gyro 55 includes a void 56 and a flange 57 that protrudes distally, thereby partially covering void 56. Distal gyro 55 also includes a flange 71 that is similar in many respects to flange 73. Flange 71 includes a channel 72 at about the midpoint of its radial protrusion. Flange 71, similar to flange 73, holds distal wire 63 while also anchoring second ball 64, so that distal wire 63 is inhibited from slipping out of channel 72 when distal gyro 55 is pulled proximally. It is noted that void 56, flange 57, recess 52, and flange 53 are annular, so they are in engagement around the circumferences of proximal gyro 51 and distal gyro 55.

Proximal gyro 51 and distal gyro 55 may be in constant engagement with one another due to their interlocking. Distal gyro 55 is interlocked around flange 53 of proximal gyro 51, such that portions of distal gyro 55 and proximal gyro 51 tightly abut one another, while also allowing rotation of distal gyro 55 or proximal gyro 51, relative to the other. Flange 57 of distal gyro 55 and flange 53 of proximal gyro 51 hook against one another, as flange 57 remains within recess 52 of proximal flange 51, and flange 53 remains within void 56 of distal gyro 55. Thus, the hook-like features of flanges 53 and 57 inhibit proximal gyro 51 and distal gyro 55 from disengaging from one another. It is noted that the dimensions of flanges 53, 57, recess 52, and void 56 are not particularly limited, and may be any suitable dimensions that allow for the above described rotatable, interlocked engagement between proximal gyro 51 and distal gyro 55.

In view of the above, rotatable gyro 50 enables the rotation of proximal steering wire 61 or distal steering wire 63, as distal portion 20 or proximal portion 10 is rotated, relative to the other. Furthermore, the above configuration of gyro 50 enables the articulation of flexible shaft 24, via steering wire 60. Proximal wire 61, including first ball 62, may be pulled via actuation of any suitable controller, e.g., device 43 (not shown), which in turn pulls on proximal gyro 51 due to first ball 62 pulling against flange 73. Pulling on proximal gyro 51 results in distal gyro 53 being pulled, due to their interlocked engagement. This, in turn, pulls on distal steering wire 63, due to flange 71 pushing against second ball 64, and results in steering wire 63 pulling on the distal end of shaft 24, thereby enabling articulation thereof.

Figure 3B:
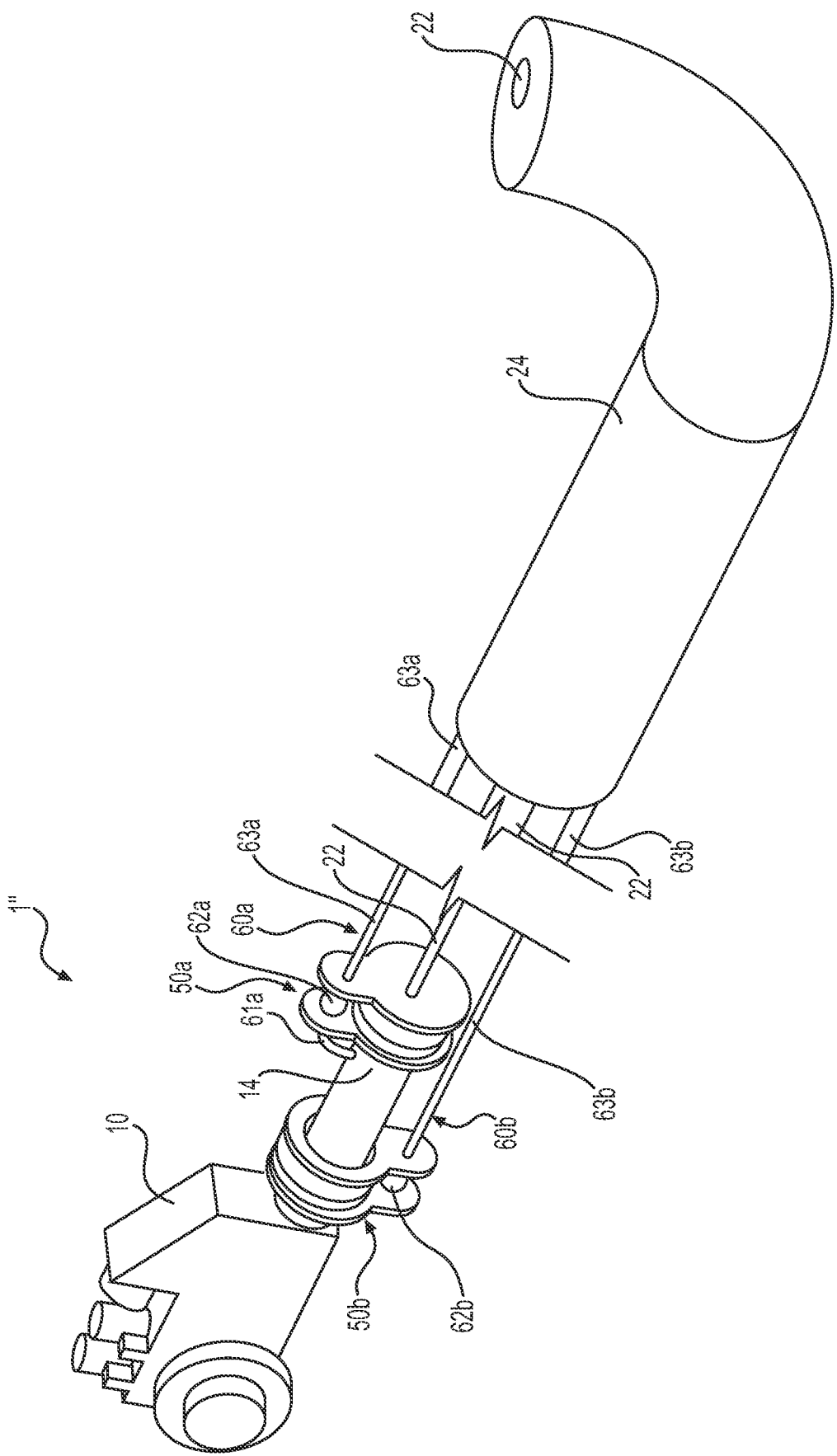
FIG. 3B is a perspective view of a medical device including a plurality of the rotatable gyros of FIG. 3A.

FIG. 3B illustrates a medical device 1″ including two rotatable gyros 50a and 50b, both of which are identical to rotatable gyro 50 of FIG. 3A. Gyros 50a and 50b respectively hold the two steering wires, 60a and 60b. It is noted that the number of gyros included in medical devices is not particularly limited, and may be any suitable number that corresponds with the number of steering wires (e.g. one, two, or four) within a medical device embodiment. As shown in FIG. 3B, one gyro, rotatable gyro 50a, may be positioned around the area in which the lumen (not shown) of guide 14 and working channel 22 meet, as described above for FIG. 3A. Meanwhile, the second gyro, rotatable gyro 50b, may be positioned proximal to gyro 50a, so that it may also be within proximal portion 10. Steering wires 60a and 60b are coupled to the distal end of shaft 24. Thus, as shaft 24 rotates, distal gyros 55a and 55b, which hold distal wires 63a and 63b, also may rotate.

Figure 4:
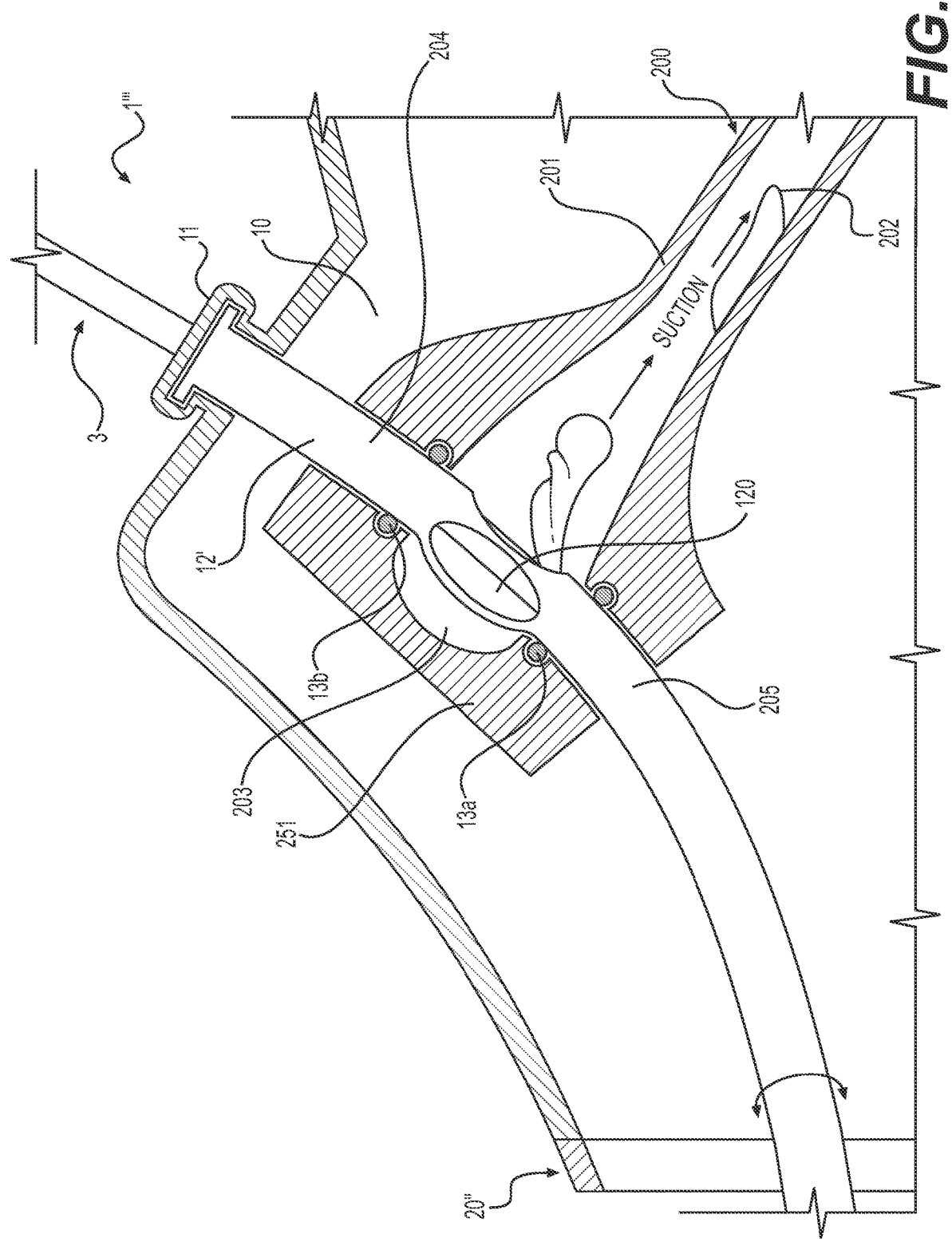
FIG. 4 is a cross-sectional view of a portion of a medical device, according to another embodiment.

Suctioning may also be enabled in medical devices that include a rotatable working channel. Medical device 1‴, as shown in FIG. 4, is similar to device 1 in some respects. Like reference numerals refer to like parts. Differences between device 1 and device 1‴ will be described below. In device 1‴, working channel 12' is a rotatable tube that extends from proximal portion 10, through rotatable distal portion 20″, to the distal end of a shaft (not shown). At least a portion of channel 12' may be fixed to the shaft. Thus, channel 12', as a whole, may rotate as distal portion 20″ and the shaft also rotate. Working channel 12' includes a plurality of circular/oval-shaped openings 120 distributed about its circumference. The number of openings 120 and the shape of openings 120 is not particularly limited. Furthermore, openings 120 are sealed from the remaining, unopened portions of working channel 12', via sealing rings 13a and 13b. Rings 13a and 13b are fitted around the portions of working channel 12' that are adjacent to openings 120, with one ring 13a distal to openings 120 and the other ring 13b proximal to openings 120. Rings 13a and 13b may be fitted around working channel 12' so that they serve as a seal, while also enabling rotation of channel 12' within rings 13a and 13b. Rings 13a and 13b may be of any suitable material used for sealing purposes, e.g., rubber.

Device 1‴ further includes a tubular suction body 200, one end of which is fitted around a portion of working channel 12'. Suction body 200 includes a tube wall 201, a lumen 202, and a cavity 203. One end of lumen 202 may be connected to a suctioning source (not shown) and/or a disposal collecting suctioned materials (not shown). The other end of lumen 202 leads to cavity 203 of tubular suction body 200, surrounding the portion of working channel 12' including openings 120. The portion of suction body 200 including cavity 203 includes proximal and distal openings 204, 205. Openings 204, 205 sheath over channel 12' and include rings 13a, 13b. In FIG. 4, the portion of suction body 200 including cavity 203 is fitted around the aforementioned portion of working channel 12', so that cavity 203 and openings 120 are sealed from the remainder of device 1‴. Thus, such a configuration enables suction body 200 to suction and remove materials, e.g., fluids, that have been captured within a portion of working channel 12' that is distal to openings 120. Said materials may exit from channel 12' through openings 120 and fall into lumen 201, via suction. The above-described configuration enables suctioning while still introducing accessory devices, e.g., accessory 3, through port 11 and working channel 12'.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
   a shaft;
   a handle including a proximal portion and a distal portion, wherein the distal portion of the handle is fixed to a proximal portion of the shaft; and
   a channel extending within the handle and extending into a lumen of the shaft, wherein the channel includes a proximal channel and a distal channel, the proximal channel being rotatable relative to the distal channel and aligned with the distal channel throughout rotation of the proximal channel,
   wherein the proximal portion of the handle includes the proximal channel, wherein the distal portion of the handle includes the distal channel, wherein the distal portion of the handle is rotatable relative to the proximal portion of the handle, and the shaft is configured to rotate with the distal portion of the handle,
   wherein the handle further includes a guide, wherein the guide includes a lumen extending along a central axis of the guide, and wherein the lumen is positioned between the proximal channel and the distal channel, and the lumen is aligned with the proximal channel and the distal channel,
   wherein an inner surface of the proximal portion of the handle includes one or more supports that extend radially inward, wherein the one or more supports are configured to anchor the guide within the proximal portion of the handle.

2. The medical device of claim 1, wherein the shaft surrounds at least a portion of the distal channel, and the distal channel is configured to rotate with the shaft and the distal portion of the handle.

3. The medical device of claim 1, wherein the distal portion of the handle is rotatable relative to the proximal portion of the handle in either a clockwise direction or a counterclockwise direction.

4. The medical device of claim 1, wherein the rotation of the distal portion of the handle is limited to a set degree of rotation.

5. The medical device of claim 1, wherein the distal portion of the handle remains stationary relative to the proximal portion of the handle by frictional forces generated between a surface of the distal portion of the handle abutting a surface of the proximal portion of the handle.

6. The medical device of claim 1, wherein the guide is fixed to an inner surface of the proximal portion of the handle.

7. The medical device of claim 1, wherein the distal portion of the handle further includes a support along an inner surface of the distal portion of the handle, and the proximal portion of the shaft is fixed to the support.

8. A medical device, comprising:
   a shaft;
   a handle including a proximal portion and a distal portion, wherein the distal portion of the handle is fixed to a proximal portion of the shaft; and
   a channel extending from the handle into the shaft, wherein the channel includes a proximal channel and a distal channel, wherein the proximal channel comprises a tube extending within a cavity of the proximal portion of the handle, and the proximal channel is rotatable relative to the distal channel and aligned with the distal channel throughout rotation of the proximal channel, wherein the proximal portion of the handle includes the proximal channel and the distal portion of the handle includes the distal channel, wherein the distal portion of the handle is rotatable relative to the proximal portion of the handle, wherein the handle further includes a guide including a lumen positioned between the proximal channel and the distal channel, and wherein the lumen is aligned with the proximal channel and the distal channel, and wherein an inner surface of the proximal portion of the handle includes one or more supports that extend radially inward, wherein the one or more supports anchor the guide within the proximal portion of the handle.

9. The medical device of claim 8, wherein the distal channel comprises a tube extending within a cavity of the distal portion of the handle and a lumen of the shaft.

10. The medical device of claim 9, wherein the lumen of the shaft surrounds at least a portion of the distal channel, and the distal channel is configured to rotate with the shaft and the distal portion of the handle.

11. The medical device of claim 9, wherein the tube is fixed to an inner surface of the shaft.

12. The medical device of claim 8, wherein the distal portion of the handle is rotatable relative to the proximal portion of the handle in either a clockwise direction or a counterclockwise direction.

13. The medical device of claim 8, wherein the distal portion of the handle remains stationary relative to the proximal portion of the handle by frictional forces generated between a surface of the distal portion of the handle abutting a surface of the proximal portion of the handle.

14. A medical device, comprising:
a shaft;
a handle including a proximal portion and a distal portion, wherein the distal portion of the handle is fixed to a proximal portion of the shaft; and
a channel extending within the handle into a lumen of the shaft, wherein the channel includes a proximal channel and a distal channel, and the proximal channel is rotatable relative to the distal channel and aligned with the distal channel throughout rotation of the proximal channel, wherein the proximal portion of the handle includes the proximal channel and the distal portion of the handle includes the distal channel, wherein the distal portion of the handle is rotatable relative to the proximal portion of the handle, and wherein the handle further includes a guide including a lumen positioned between the proximal channel and the distal channel, and wherein the handle includes one or more supports extending radially inward from an inner surface of the proximal portion of the handle to the guide, wherein the one or more supports anchor the guide within the proximal portion of the handle.

15. The medical device of claim 14, wherein the guide is tubular or cylindrical.

16. The medical device of claim 14, wherein the distal channel comprises a tube extending within a cavity of the distal portion of the handle and the lumen of the shaft.

17. The medical device of claim 14, wherein the distal channel is fixed to an inner surface of the shaft.

18. The medical device of claim 14, wherein a diameter of the proximal channel is equal or about equal to the diameter of the distal channel.

19. The medical device of claim 14, wherein the distal portion of the handle further includes a clamp along an inner surface of the distal portion of the handle, and the proximal portion of the shaft is fixed to the clamp.

20. The medical device of claim 14, wherein each of the proximal portion of the handle and the distal portion of the handle is configured to rotate relative to an instrument extending through the proximal channel and the distal channel.

\* \* \* \* \*